United States Patent [19]

Buysch et al.

[11] Patent Number: 5,068,321
[45] Date of Patent: Nov. 26, 1991

[54] CARBONIC ACID ESTERS OF POLYSACCHARIDES AND A PROCESS FOR THEIR PRODUCTION

[75] Inventors: Hans-Josef Buysch; Alexander Klausener, both of Krefeld; Klaus Szablikowski; Klaus Balser, both of Walsrode; Michaela Wilke, Schneverdingen, all of Fed. Rep. of Germany

[73] Assignee: Wolff Walsrode Aktiengesellschaft, Walsrode, Fed. Rep. of Germany

[21] Appl. No.: 420,841

[22] Filed: Oct. 13, 1989

[30] Foreign Application Priority Data

Oct. 27, 1988 [DE] Fed. Rep. of Germany ....... 3836600

[51] Int. Cl.$^5$ ..................... C08B 3/00; C08B 31/04; C08B 37/00
[52] U.S. Cl. ........................ 536/32; 536/48; 536/58; 536/63; 536/107
[58] Field of Search ..................... 536/32, 48, 58, 63, 536/107

[56] References Cited

U.S. PATENT DOCUMENTS 3,284,442 11/1966 Jarowenko et al. .................. 536/32
3,705,890 12/1972 Barker et al. .......................... 536/50
3,810,821 5/1974 Barker et al. .......................... 536/50
4,097,667 6/1978 Holst et al. ............................ 536/50

FOREIGN PATENT DOCUMENTS 2073901 10/1971 France .
2335525 12/1975 France .

OTHER PUBLICATIONS

European Search Report.

Primary Examiner—Nathan M. Nutter
Attorney, Agent, or Firm—Sprung Horn Kramer & Woods

[57] ABSTRACT

New polysaccharide carbonates are produced by acylation of polysaccharides with carbonic acid esters and have degrees of substitution of preferably 0.5 to 3.

11 Claims, No Drawings

CARBONIC ACID ESTERS OF POLYSACCHARIDES AND A PROCESS FOR THEIR PRODUCTION

This invention relates to new carbonic acid esters of polysaccharides having a degree of substitution (DS) of 0.5 and higher and to a process for their production.

Carbonic acid esters of polysaccharides are interesting starting products for the production of other modified polysaccharides, particularly carbamates having various properties. One particularly topical application is in the production of depots for bioactive material (cf. Makromol. Chem. 186, 17–29 (1985)) and in the fixing of enzymes for carrying out enzymatic reactions in heterogeneous phase (cf. for example J.C.S. Perkin I 1974, 757–762 or Biochemistry Internat. 4 (1982) 629–635). Accordingly, there has been no shortage of attempts to produce carbonic acid esters of various polysaccharides. The applications mentioned above, more especially the fixing of enzymes, require a high DS to guarantee a high enzyme density on the polysaccharide, high activity and low catalyst volumes for the enzymatic reactions.

The majority of conventional processes operate in homogeneous phase, i.e. with dissolved polysaccharide, and generally give polysaccharides having only a low degree of substitution. In addition, the reaction in homogeneous phase involves serious problems on account of the often very high viscosity of such solutions and the resulting need to use large amounts of solvents during the reaction and precipitation of the reacted polymers.

According to E. Heuser and F. Schneider, Ber. deut. chem. Ges. 57, 1389–1392 (1924), the homogeneous reaction of hydrocellulose obtained from viscose in 8% sodium hydroxide is said to give a methyl carbonate cellulose having a DS of at most 2, although unfortunately this is a random result on account of the presence of the hydrolyzing sodium hydroxide and cannot be reproduced. The yields are always below 20%. Accordingly, this process is of no use whatever.

Starch, dextrin and dextran (Carbohydrate Research 8 (1968), 266–274) can be converted into carbonate polysaccharides up to a maximum DS of 0.4 in solutions of dimethyl sulfoxide. According to Carbohydrate Research 17 (1971), 471-4, heterogeneous reactions of cellulose in dimethyl sulfoxide or dimethyl formamide can be shown by spectroscopic analyses to lead to a DS of around 0.5. However, the nitrogen value of 0.8 to be determined after reaction of the carbonate with $NH_3$ to the carbamate suggests a considerably lower DS of <0.2.

According to J.C.S. Perkin I 1973, 2293–2299, macroporous cellulose, likewise in suspension in dimethyl sulfoxide, leads after reaction with chlorocarbonic acid ethyl ester to a cellulose carbonate having a DS of <0.5 (as calculated from the maximum $NH_3$ uptake of 3 mmol/g matrix).

Dextrans can be highly substituted up to a DS of 3.0 in a solution of dimethyl formamide containing LiCl by reaction with chlorocarbonic acid ethyl or butyl ester in the presence of various bases, cf. Makromol. Chemie (1985), 17-29, although this DS was calculated from spectroscopic data. Expression of the carbonate content in mol-% suggests considerably lower degrees of substitution of at most 1.5. It is pointed out in this publication that the reaction rate and the degree of substitution depend upon the basicity of the auxiliary base used. Accordingly, the best results are obtained with triethylamine. Despite the high degrees of substitution, this process is unsuitable for application on an industrial scale for the reasons explained above on account of the complex solvent mixture and the resulting difficulties involved in working up. In addition, the acyl halides undergo decomposition under the reaction conditions.

If aromatic chlorocarbonic acid esters, for example the p-nitrophenyl ester, are used and if the reaction is carried out in dimethyl sulfoxide as solvent for dextran, a much lower DS of approximately 0.3 is obtained, as calculated from the percentage activation of at most 30% (number of carbonate groups per 100 anhydroglucose units). In addition, it was found that the number of carbonate groups passes through a maximum during the reaction, i.e. the carbonate group is not stable under the reaction conditions (Makromol. Chem. 186, 2455 to 2460 (1985)).

The same applies to reactions with aromatic chlorocarbonic acid esters on Sepharose gel suspended in an anhydrous pyridine/acetone mixture (Biochemistry International 4 (1982), 629–635). Only a low DS of up to 0.28 is obtained (as calculated from the reference to at most 1.8 mmol active groups per g polymer).

There is at present no process by which highly substituted polysaccharide carbonates could be produced in heterogeneous phase, i.e. with relatively high concentrations of polysaccharide, while avoiding highly viscous solutions. In particular, there are no processes for the production of highly substituted aromatic polysaccharide carbonates which contain carbonate bonds of different reactivity and are particularly suitable for further substitution reactions. Nevertheless, there is considerable commercial interest in such polymers (Carbohydrate Research 26 (1973), 401 to 408, pages 402 and 407).

Accordingly, the problem addressed by the present invention is to provide new highly substituted polysaccharide carbonates.

Accordingly, the present invention relates to polysaccharide carbonates containing recurring units corresponding to formula I

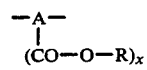

in which
A is a monosaccharide unit,
R is an aliphatic or cycloaliphatic radical containing 1 to 18 carbon atoms, an araliphatic radical containing 7 to 12 carbon atoms, an aromatic radical containing 6 to 12 carbon atoms optionally substituted by halogen, $NO_2$, phenyl, $COOR^1$, $OR^1$ or an aromatic radical containing 6 to 12 carbon atoms substituted by a $C_{1-6}$ aliphatic group,
$R^1$ is a $C_{1-4}$ alkyl radical and
x is a number of 0.5 to 3.0.
In a preferred embodiment,
R is an aliphatic radical containing 1 to 6 carbon atoms, an aromatic radical containing 6 to 10 carbon atoms optionally substituted by Cl, $CH_3$, $NO_2$, $OCH_3$ and $COOCH_3$ and
x is a number of 0.8 to 3.0,
A is a monosaccharide unit derived from a hexose or pentose.
In a particularly preferred embodiment, R represents CH$_3$, C$_2$H$_5$, phenyl, chlorophenyl, nitrophenyl and naphthyl and x is a number of 1.0 to 3.0;

more particularly,

R is phenyl and x is a number of 1.0 to 3.0.

The present invention also relates to a process for the production of polysaccharide carbonates by reaction of polysaccharides with carbonic acid esters, preferably chlorocarbonic acid ester, in the presence of a base, characterized in that, optionally after pretreatment with the base, the polysaccharide is reacted in heterogeneous phase with carbonic acid ester for preferably at least 3 hours at temperatures of preferably 10° to 120° C. in the presence of preferably at least 0.5% by weight moisture, based on the polysaccharide.

The present invention also relates to polysaccharide carbonates prepared by acylation of polysaccharides with carbonic acid esters in heterogeneous phase in the presence of a base, characterized in that the polysaccharide carbonates have a degree of substitution of 0.5 to 3.0, based on the monosaccharide unit, in that at most 20% by weight of the polysaccharide carbonates are soluble in chloroform at 20° C. and in that at most 30% of the carbonate groups are cyclic.

On the basis of the prior art, this must be regarded as surprising in more than one respect. First, high carbonate contents can only be obtained in exceptional cases, even in a homogeneous solution of polysaccharides. The aromatic carbonates which, hitherto, were clearly particularly difficult to obtain can be produced particularly readily despite the greater space occupied by the aromatic radicals. On the basis of the consistent procedures (low temperature, short reaction time) hitherto adopted by researchers and the decomposition which the carbonates and the chlorocarbonic acid esters have now been found to undergo, the conditions according to the invention could not have been expected to produce any carbonate substitution let alone high degrees of substitution. It is also surprising that no cyclic carbonates are formed, something which is clearly difficult to avoid on the basis of existing results. Aromatic carbonates in particular should readily be converted into cyclic carbonates on account of the loose binding of the aromatic part.

Suitable starting materials for the production of the polysaccharide carbonates according to the invention are, for example, polyglucosans, such as cellulose, the various derivatives of cellulose, such as methyl cellulose, or mixed cellulose ethers, such as methyl hydroxyethyl celluloses, carboxymethyl cellulose, the various salts thereof with sodium, potassium, calcium or ammonium ions, particularly quaternary ammonium ions; cellulose sulfate containing various counterions, for example of sodium, potassium, calcium, ammonium and quaternary ammonium groups; starch, dextrins, glycogen; polyfructosans, such as inulin and graminin; polymannosans, polygalactosans; mixed polysaccharides, such as hemicelluloses, also polyxylosans and polyarabinosans and also heteropolysaccharides, such as gellan, xanthan and pullulan. Preferred starting materials are cellulose and cellulose derivatives, starch and dextrins, particularly preferred starting materials being cellulose, methyl cellulose, ethyl cellulose, hydroxyethyl cellulose, hydroxypropyl cellulose, carboxymethyl cellulose and salts thereof and starch.

Suitable carbonic acid esters are in particular those corresponding to the following general formula

in which

R is as defined for formula (I),

X represents bromine, azole, particularly triazole, imidazole, pyridinium, more especially chlorine.

Suitable bases for the production of the polysaccharide carbonates according to the invention are tertiary nitrogen bases from the aliphatic, aromatic and heterocyclic series, such as trimethylamine, triethylamine, tributylamine, dimethyl cyclohexylamine, diisopropyl ethylamine, dicyclohexyl methylamine, dimethyl-β-methoxyethylamine, N,N,N',N'-tetramethyl ethylenediamine, N,N,N',N'-tetramethyl-β,β'-diaminodiethyl ether, N,N'-dimethyl piperazine, N-methyl morpholine and diazabicyclooctane, tetramethyl ethylenediamine, N,N-dimethyl aniline, N,N-diethyl aniline, N,N,N',N'-tetramethyl diaminobenzene, N,N-dimethyl toluidine, N,N-dimethyl xylidine, N,N-dimethyl anisidine and N-phenyl morpholine, pyrazole, N-alkyl pyrazole, imidazole, N-methyl imidazole, triazole, N-ethyl triazole, N,N-dimethylaminoimidazole, N,N-diethylaminotriazole, pyridine, α-, β-, γ-picoline, the lutidines, collidine, ethyl methyl pyridines, N,N-dialkylaminopyridines, such as N,N-dimethyl-4-aminopyridine, quinoline, methyl quinoline and isoquinoline.

Preferred bases are triethylamine, dimethyl cyclohexylamine, methyl morpholine, dimethyl piperazine and diazabicyclooctane, tetramethyl ethylenediamine, N,N-dimethyl aniline and N,N-dimethyl anisidine, imidazole, N-methyl imidazole, N,N-dimethylaminoimidazole, pyridine, quinoline and the methyl and ethyl pyridines, particularly preferred bases being pyridine and the methyl pyridines.

The molar ratio of carbonic acid ester to monosaccharide unit is variable and depends on the degree of substitution to be obtained. In general, the molar ratio should be at least 0.8:1. Accordingly, an excess of carbonic acid ester per mol saccharide unit should be used to obtain relatively high degrees of substitution. The molar ratio may be up to 10:1. In many cases, however, this is not economical so that ratios of 0.8:1 to 6:1 and preferably from 1:1 to 4:1 are used.

Degrees of substitution below 0.5 may of course also be obtained by the process according to the invention. To this end, correspondingly smaller quantities of carbonic acid ester should be used or the reaction times should be shortened.

The molar ratio of base to carbonic acid ester should be at least 1:1. It is also possible to use an excess of base so that the molar ratio of base to chlorocarbonic acid ester may be between about 1:1 and 10:1. It is thus possible to carry out the reaction without an additional dispersion medium in an excess of the base.

Accordingly, the reaction may be carried out with and without additional dispersion medium. Suitable dispersion media are solvents that are inert under the reaction conditions, such as aliphatic and aromatic hydrocarbons, halogenated hydrocarbons, ethers, esters, ketones, carboxylic acid amides and carboxylic acid nitriles.

Examples of suitable dispersion media are cyclohexane, pentane, heptane, isooctane, benzene, toluene, methylene chloride, chloroform, dichloroethane, trichloroethylene, chlorobenzene, dichlorobenzene, bromobenzene, diethyl ether, diisopropyl ether, dibutyl ether, dioxane, benzodioxane, anisole, dimethoxybenzene, ethylene glycol dimethyl ether, diethylene glycol dimethyl ether, acetic acid ethyl ester, acetic acid butyl ester, propionic acid ethyl ester, butyric acid ethyl ester, benzoic acid ethyl ester, malonic acid diethyl ester, succinic acid diethyl ester, acetone, methyl ethyl ketone, diethyl ketone, methyl isopropyl ketone, acetophenone, cyclohexanone, formamide, methyl formamide, dimethyl formamide, dimethyl acetamide, tetramethyl urea, N,N-dimethyl ethylene urea, N,N-dimethyl-2,6-diaza-4-oxacyclohexanone, N-methyl pyrrolidone, N-methyl caprolactam, acetonitrile, propionitrile, butyronitrile, benzonitrile, adiponitrile, $\beta$-methoxypropionitrile and $\beta$-cyano-$\beta'$-methoxydiethyl ether.

The quantity of dispersion medium should be gauged in such a way that a readily stirrable suspension is formed.

Starting materials, reagents, bases and solvents should be substantially anhydrous. Accordingly, the reactants and dispersion media have to be freed from excess water or a correspondingly larger quantity of chlorocarbonic acid ester has to be used to compensate for excess water. However, this is not an economical procedure. It is of greater advantage to dry the starting materials as a whole using typical agents and methods, for example at elevated temperature in vacuo, by azeotropic distillation, by drying over alkali hydroxides, such as NaOH or KOH, or alkaline earth hydroxides or oxides, such as $Ca(OH)_2$ or CaO, over dehydrated salts, such as sodium sulfate or copper sulfate, or over molecular sieves which may readily be regenerated. If the water is removed to such an extent that the polysaccharides only contain the non-removable bound water, the reproducibility of the reaction is jeopardized, so that at least 0.5% by weight, based on the polysaccharide to be reacted, is used. An upper limit is imposed on the addition of water by economic considerations because part of the acylating agent is lost, so that generally 0.5 to 5% by weight, preferably 0.8 to 4.0% by weight and, more preferably, 1.0 to 3.0% by weight is added. The water of crystallization content of polysaccharides is variable and may be determined by suitable analytical methods (cf. "Starch Chemistry and Technology", ed. by R. L. Whistler, J. N. Bemiller, E. F. Paschall, 1983, sec. Ed., pages 214 to 219, Academic Press Inc., N.Y.).

The moisture content of cellulose is determined by the analytical method of the Verein der Zellstoff- und Papier-Chemiker und -Ingenieure, Merkblatt IV/42/67 of 23.10.1967.

For cellulose, it is between 2 and 4% by weight for example, depending on type and origin. Information on bound water or moisture content can be found in the relevant literature (cf. K. Gotze: Chemiefasern, Vol. 1, page 264, 3rd Edition, 1964, Springer Verlag).

Since the ester is generally anhydrous, the missing quantity of water is generally added to the polysaccharide suspension before addition of the ester. The reaction is best carried out by initially introducing the polysaccharide with the base, optionally additional water and, optionally, the dispersion medium which does not dissolve the polysaccharide, optionally subjecting the polysaccharide to a pretreatment, depending on type, and then adding the carbonic acid ester.

A pretreatment is best carried out when the polysaccharide is to be digested for the reaction, as in the case of cellulose. The temperature may vary between 10° and 120° C. and is not critical. The pretreatment time is also not critical and may be between several minutes and many hours. In general, the pretreatment time is between 1 and 30 h. However, the pretreatment is not compulsory because the necessary digestion may also take place during the reaction.

Polysaccharides pretreated with aqueous alkali hydroxide and then freed from alkali hydroxide and excess water may also be introduced into the reaction. This can be of advantage in individual cases, particularly with celluloses, and can increase the degree of substitution a little further by virtue of the better digestion. 8 to 25% sodium hydroxides are particularly suitable for this purpose being subsequently washed out with water and the water with alcohols, such as isopropanol, or the auxiliary base. The alcohol may be removed by drying or displacement with the solvent used for the reaction.

The carbonic acid ester is added at such a rate that the heat generated can be dissipated under control.

The reaction temperature is generally in the range from 10° to 120° C., preferably in the range from 15° to 100° C. and more preferably in the range from 20° to 90° C. The more sensitive the polysaccharide, the lower the reaction temperature should be.

The reaction time depends upon the type of polysaccharide and upon the temperature selected. The better the polysaccharides are digested, the shorter the reaction time can be. In order to obtain an adequate DS, however, the reaction time should not be less than 3 h. In contrast to the literature data discussed in the foregoing, longer reaction times are not harmful and generally lead to a further increase in the DS. Accordingly, an extended reaction time is recommended for substantially complete utilization of the acylating agent, although this should of course be viewed in conjunction with other economic factors and possible damage to sensitive polysaccharides.

The polysaccharide carbonates are worked up by methods known per se according to the nature of the reacted polysaccharide. Working up is made particularly simple if, after separation of the liquid part of the reaction mixture, the reaction product can be freed from adhering residues of the reaction mixture by washing with suitable inert solvents. The solvent used should neither dissolve nor swell the reaction product. Suitable solvents must be determined from case to case by means of preliminary tests. In many cases, the solvents mentioned above may be used. Alcohols or water may also frequently be used.

The polysaccharide carbonates according to the invention produced by the process according to the invention have degrees of substitution of 0.5 to 3.0, preferably 0.8 to 3.0 and, more preferably, 1.0 to 3.0. If desired, polysaccharide carbonates having relatively low degrees of substitution of less than 0.5 to 0.1 may of course also be produced by the process according to the invention.

The polysaccharide carbonates according to the invention, particularly the phenyl carbonates, are excellent starting products for the production of various other derivatives, particularly for the production of carbamates, and for the fixing of catalytically active species, for example enzymes. They may also be converted by reaction with polyamines into basic polysaccharides which are suitable for use as basic ion exchangers. Basic polysaccharides such as these may also be converted by reaction with alkylating agents into polysaccharides containing quaternary ammonium groups.

The high degrees of substitution of the carbonates provide for correspondingly high degrees of substitution in carbamate formation and in cationization and, hence, for greater efficiency in practical application. However, cationic polysaccharides are desirable filter aids for medical filters, auxiliaries for paper manufacture, additives for cosmetic cleansing preparations, flocculating agents for wastewater treatment (cf. also M. Langer, Wochenblatt für Papierfabrikation 1978 (18), 690 to 693).

Depending on the polysaccharide used, both insoluble, solid and also soluble, basic or cationic polysaccharides may be produced by the method described above.

Where high molecular weight celluloses for example are used as starting material, insoluble products of fibrous structure are obtained, being eminently suitable for the production of filter materials or for fixing enzymes.

Soluble products may be obtained from starch for example. The same applies to polysaccharides of relatively low molecular weight, such as dextrins. Soluble, basic and cationic products may also be obtained from cellulose ethers. Methyl cellulose, ethyl cellulose and carboxymethyl cellulose for example are suitable for this purpose.

Soluble products of the type in question may be used with advantage for paper manufacture, as flocculating agents and for cleansing preparations.

The polysaccharide carbonates according to the invention are eminently suitable for further reactions, above all for the production of carbamates and also basic polysaccharide urethane amines. More particularly, the basic polysaccharides thus produced are eminently suitable for the production of cationic polysaccharides.

EXAMPLES

Remarks

The quantities of polysaccharide in mol are based on the monomer unit. Although not specifically mentioned, all reactions are carried out on suspended, non-dissolved polysaccharide. Elemental analyses are generally carried out on samples dried in vacuo at 105° C.

EXAMPLE 1

A suspension of 200 g (~1.25 mol) of an air-dry, commercially available spruce cellulose having a moisture content of 6 to 7% by weight in 900 g pyridine dried over KOH and 2.5 l benzene dried over $CaCl_2$ was stirred for 20 h at room temperature, after which 785 g (5.0 mol) phenyl chlorocarbonic acid ester were added dropwise over a period of 3 h at room temperature, followed by stirring for 70 h at room temperature and then for another 6 h at 80° C. After cooling and filtration under suction, the product was thoroughly washed once with benzene, twice with isopropanol and three times with water and dried in vacuo for 3 h at 105° C. Yield: 656 g of a dry powder.

Elemental analysis: C 60.7%, H 4.3%, O 32.6%.

The DS is approximately 3.

EXAMPLE 2

106 g (~0.5 mol) of a hydroxyethyl cellulose having a water content of 6.5% by weight and a DS of 1.1 are suspended in 1 l benzene and 198 g (2.5 mol) pyridine (both dried) and, after stirring for 20 h at 50° C., 392 g (2.5 mol) chlorocarbonic acid phenyl ester are added to the resulting suspension over a period of 2 h. After stirring for another 20 h at 80° C., the product is cooled, filtered under suction, washed with benzene and isopropanol until salt-free and dried in a high vacuum at 50° C. to constant weight. Yield: 260 g. DS 2.4.

Elemental analysis: C 59.4% H 4.7% (starting product: 46.2% 75%)

IR spectrum: strong carbonate-CO-band at 1770 $cm^{-1}$

EXAMPLE 3

A mat of long-fiber, commercially available cellulose is fragmented and swollen overnight in water, after which the flocks are size-reduced in a Starmix, filtered under suction and pressed, dried in vacuo for about 40 h at 105° C. to constant weight and any flocks still present are reduced to fibers in the Starmix.

81 g (0.5 mol) of the cellulose thus prepared are suspended in 1.5 l methylene chloride and 158 g (2.0 mol) pyridine (both dried over Baylith T 144, a zeolite A, manufactured by Bayer AG) after addition of 2.5 g (0.14 mol) water and the resulting suspension pretreated for 20 h at room temperature. 235.5 g (1.5 mol) chlorocarbonic acid phenyl ester are added dropwise over a period of 3 h at 20° to 25° C. and the mixture then stirred for 20 h at 25° C. and for 5 h at 45° C. After cooling, pressing and washing with methylene chloride in isopropanol, the filter residue is dried in vacuo at 50° C. to constant weight. Yield: 141 g fibrous material.

Elemental analysis: C 55.0% H 5.1%

DS 1.0 to 1.2

If this experiment with the highly dried cellulose is repeated without the addition of water, no reaction takes place.

EXAMPLE 4

314 g (2.0 mol) chlorocarbonic acid phenyl ester are added dropwise over a period of 3 h at room temperature to a suspension of 183 g (1 mol) methyl cellulose (4 to 5% $H_2O$) having a degree of substitution of 1.4 in 316 g (4.0 mol) pyridine and 2.0 l methylene chloride (both dried with the molecular sieve Baylith T 144), which has been stirred for 15 h at room temperature. After stirring for 20 h at 20° to 25° C., the suspension is filtered under suction, washed with methylene chloride and isopropanol until salt free and dried in vacuo at 50° C. to constant weight. 316 g of a loose material having a DS of 1.3 are obtained.

Elemental analysis: C 58.6% H 5.29% (methyl cellulose: 49.2% 7.1%)

EXAMPLE 5

109 g (1.0 mol) chlorocarbonic acid ethyl ester are added dropwise over a period of 3 h at room temperature to a suspension of 46 g (0.25 mol) methyl cellulose (DS 1.4; approx. 5% $H_2O$) in 800 ml benzene and 79 g pyridine (1.0 mol), which has been stirred for 15 h at 25° C. After 5 h at 22° to 25° C., the suspension is filtered under suction, washed with benzene and isopropanol until free from chloride and dried in vacuo at 50° C. to constant weight. Yield: 67 g. DS 1.0.

Elemental analysis: C 48.6% H 6.6%

IR spectrum: strong carbonate-CO-band at 1770 $cm^{-1}$

EXAMPLE 6

47 g (0.30 mol) chlorocarbonic acid phenyl ester are added dropwise over a period of 3 h to a suspension of 183 g (1.0 mol) methyl cellulose (approx. 5% $H_2O$, DS 1.4), 316 g (4.0 mol) pyridine and 1.5 l methylene chloride (both dried with zeolite A) and is stirred for 20 h at 25° C and for 5 h at 45° C. A yield of 210 g is obtained after working up with methylene chloride and isopropanol and drying at 50° C.

EXAMPLE 7

162 g (1.0 mol) spruce cellulose (6% $H_2O$) are treated for 3 h with 18% NaOH, filtered under suction, washed with water until free from alkali and then with pyridine until free from water. 314 g (2 mol) chloroformic acid phenyl ester are added over a period of 2 h to the suspension in pyridine. After 12 h at 80° C., the suspension is filtered under suction, washed with isopropanol or water and dried in vacuo at 50° C. Yield: 439 g, DS approx. 2.

EXAMPLE 8

53 g (0.25 mol) hydroxyethyl cellulose (6–7% $H_2O$, DS 1.1), 100 g pyridine and 100 g chlorocarbonic acid phenyl ester are stirred in benzene for 24 h at 20° C. and for 5 h at 80° C. After filtration under suction, the product is washed with isopropanol and dried in vacuo at 50° C. Yield: 100 g. DS 1.3–1.4.

Elemental analysis: C 55.3% H 6.5%

EXAMPLE 9

290 g (1.85 mol) chlorocarbonic acid phenyl ester are added dropwise over a period of 4 h to 100 g (0.625 mol) starch which has been stirred for 24 h at room temperature in 197.5 g (2.5 mol) pyridine and 1 l benzene, followed by stirring for 10 h at room temperature and then for 20 h at 80° C. Filtration under suction, washing with isopropanol/water (1:2) and drying in a high vacuum produce a pale pink-colored solid in a yield of 200 g. DS 1.5.

Elemental analysis: C 58.9% H 4.5%

IR spectrum: strong carbonate-CO-band

EXAMPLE 10

46 g (0.25 mol) of a methyl cellulose containing approx. 5% water and having a DS of 1.0, 79 g (1.0 mol) pyridine and 600 ml chloroform are stirred for 15 h at 65° C., followed by the dropwise addition over a period of 3 h at 10° C. of 157 g (1.0 mol) chlorocarbonic acid phenyl ester. After stirring for 13 h at 50° to 60° C., the product is filtered under suction, washed until free from chloride and dried. Yield: 106 g. DS 2.0.

Elemental analysis: C 60.2% H 4.3%

We claim:

1. Polysaccharide carbonates containing recurring units corresponding to the following general formula

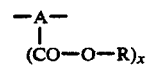

in which

A is a monosaccharide unit,

R is an aliphatic or cycloaliphatic radical containing 1 to 18 carbon atoms, an araliphatic radical containing 7 to 12 carbon atoms, an aromatic radical containing 6 to 12 carbon atoms optionally substituted by halogen, $NO_2$, phenyl, $COOR^1$, $OR^1$ or an aromatic radical containing 6 to 12 carbon atoms substituted by a $C_{1-6}$ aliphatic group, $R^1$ is a $C_{1-4}$ alkyl radical and x is a number of 0.5 to 3.0, at most 20% by weight of the polysaccharide carbonates being soluble in chloroform at 20° C. and at most 30% of the carbonate groups being cyclic carbonate groups.

2. Polysaccharide carbonates as claimed in claim 1, characterized in that

R is an aliphatic radical containing 1 to 6 carbon atoms, an aromatic radical containing 6 to 10 carbon atoms optionally substituted by Cl, $CH_3$, $NO_2$, $OCH_3$ and $COOCH_3$ and x is a number of 0.8 to 3.0.

3. Polysaccharide carbonates as claimed in claim 1, characterized in that

R represents $CH_3$, $C_2H_5$, phenyl, chlorophenyl, nitrophenyl and naphthyl and x is a number of 1.0 to 3.0.

4. Polysaccharide carbonates as claimed in claim 1, characterized in that

R represents phenyl and x is a number of 1.0 to 3.0.

5. Polysaccharide carbonates as claimed in claim 1, characterized in that A is a hexose or pentose unit.

6. Polysaccharide carbonates as claimed in claim 1, characterized in that the saccharide units A are attached to cellulose or derivatives thereof.

7. A process for the production of polysaccharide carbonates by reaction of polysaccharides with carbonic acid esters in the presence of a base, characterized in that the polysaccharides are reacted in heterogeneous phase with at least one carbonic acid ester in the presence of water.

8. A process according to claim 7, wherein prior to reaction of the polysaccharide with the carbonic acid ester the polysaccharide is pretreated with the base.

9. Polysaccharide carbonates produced by acylation of polysaccharides with carbonic acid esters in heterogeneous phase in the presence of a base, characterized in that the polysaccharide carbonates have a degree of substitution of 0.5 to 3.0, based on the monosaccharide unit, at most 20% by weight of the polysaccharide carbonates are soluble in chloroform at 20° C. and at most 30% of the carbonate groups are cyclic.

10. Polysaccharide carbonates as claimed in claim 9, characterized in that the carbonic acid ester corresponds to the following formula

in which

R is an aliphatic or cycloaliphatic radical containing 1 to 18 carbon atoms, an araliphatic radical containing 7 to 12 carbon atoms, an aromatic radical containing 6 to 12 carbon atoms optionally substituted by halogen, $NO_2$, phenyl, $COOR^1$, $OR^1$ or an aromatic radical containing 6 to 12 carbon atoms substituted by a $C_{1-6}$ aliphatic group, $R^1$ represents $C_{1-4}$ alkyl and X represents bromine, azole, particularly triazole, imidazole, pyridinium, more especially chlorine.

11. Polysaccharide carbonates as claimed in claim 9, characterized in that the carbonic acid ester is a chlorocarbonic acid ester.

* * * * *